United States Patent
Ryklin (10) Patent No.: US 7,833,956 B2
(45) Date of Patent: Nov. 16, 2010

(54) WATER COMPATIBLE EMOLLIENT FOR CLEANSING PRODUCTS

(75) Inventor: Irma Ryklin, Buffalo Grove, IL (US)

(73) Assignee: Stepan Company, Northfield, IL (US)

( * ) Notice: Subject to any disclaimer, the term of this patent is extended or adjusted under 35 U.S.C. 154(b) by 39 days.

(21) Appl. No.: 12/162,875

(22) PCT Filed: Mar. 27, 2007

(86) PCT No.: PCT/US2007/007516

§ 371 (c)(1),
(2), (4) Date: Nov. 21, 2008

(87) PCT Pub. No.: WO2007/126778

PCT Pub. Date: Nov. 8, 2007

(65) Prior Publication Data

US 2009/0181873 A1    Jul. 16, 2009

Related U.S. Application Data

(60) Provisional application No. 60/786,967, filed on Mar. 28, 2006.

(51) Int. Cl.
| | |
|---|---|
| C11D 1/00 | (2006.01) |
| C11D 1/83 | (2006.01) |
| C11D 1/86 | (2006.01) |
| C11D 3/20 | (2006.01) |
| C11D 3/37 | (2006.01) |
| A61K 8/33 | (2006.01) |
| A61K 8/34 | (2006.01) |
| A61K 8/86 | (2006.01) |

(52) U.S. Cl. .................. 510/155; 510/119; 510/147; 510/421; 510/426; 510/475; 510/483; 424/401; 424/70.11; 424/70.19

(58) Field of Classification Search .................. 510/119, 510/147, 155, 421, 426, 475, 483; 424/401, 424/70.11, 70.19

See application file for complete search history.

(56) References Cited

U.S. PATENT DOCUMENTS

| | | | |
|---|---|---|---|
| 3,929,678 A | 12/1975 | Laughlin et al. | |
| 4,199,483 A | 4/1980 | Jones | |
| 4,228,044 A | 10/1980 | Cambre | |
| 4,664,835 A | 5/1987 | Grollier et al. | |
| 5,310,508 A | 5/1994 | Subramanyam et al. | |
| 5,646,100 A | 7/1997 | Haugk et al. | |
| 5,705,147 A | 1/1998 | Shapiro et al. | |

(Continued)

OTHER PUBLICATIONS

Stepan Company, Stepan Facial Cleanser Formulation No. 1059 Product Literature, Jan. 25, 2006, pp. 1-2.*

(Continued)

Primary Examiner—Brian P Mruk
(74) Attorney, Agent, or Firm—McAndrews, Held & Malloy, Ltd.

(57) ABSTRACT

A cleansing composition comprising a water-compatible emollient that provides enhanced skin-feel characteristics, as well as viscosity-building properties. The water-compatible emollient is an alkoxylated derivative of glyceryl cocoate containing both propylene oxide and ethylene oxide groups in the molecular structure. The cleansing composition also comprises one or more surfactants, and optional additives, and can be formulated into a body wash, shampoo, facial cleanser, liquid hand soap, dish detergent or car wash detergent.

22 Claims, 8 Drawing Sheets

U.S. PATENT DOCUMENTS

| | | | |
|---|---|---|---|
| 6,156,298 | A | 12/2000 | Karlen et al. |
| 2005/0107273 | A1 | 5/2005 | Hourigan |

OTHER PUBLICATIONS

Stepan Company, Stepan Clear Conditioning Shampoo Formulation No. 1057 Product Literature, Jan. 26, 2006, pp. 1-2.*

Stepan Company, Stepan Clear Body Wash Formulation No. 977 Product Literature, Jan. 26, 2006, pp. 1-2.*

European Search Report corresponding to European Patent Application Serial No. 07754087.0-2114, mailed Feb. 26, 2009.

Stepan Company, "Stepan Facial Cleanser Formulation No. 1059 Product Literature." Jan. 25, 2006, p. 1.

Stepan Company, "Stepan Clear Conditioning Shampoo Formulation No. 1057 Product Literature." Jan. 26, 2006, p. 1.

Stepan Company, "Stepan Clear Body Wash Formulation No. 977 Product Literature." Jan. 26, 2006, p. 1.

International Search Report and Written Opinion of the International Search Authority for related PCT/ US07/07516 Application mailed Sep. 26, 2007; 6 pages.

Stepan Company, Stepan facial Cleanser Formulation No. 1059 Product Literature, Jan. 25, 2006; 2pages.

Stepan Company, Stepan Clear Conditioning Shampoo Formulation No. 1057 Product Literature, Jan. 26, 2006; 2 pages.

Stepan Company, Stepan Clear Body Wash Formulation No. 977 Product Literature, Jan. 26, 2006; 2 pages.

* cited by examiner

WATER COMPATIBLE EMOLLIENT FOR CLEANSING PRODUCTS

RELATED APPLICATIONS

This patent application makes reference to, claims priority to and claims benefit from U.S. Provisional Patent Application Ser. No. 60/786,967 filed on Mar. 28, 2006.

FIELD OF THE INVENTION

The presently described technology relates to cleansing compositions. More particularly, the presently described technology relates to improved alkoxylated derivatives of glyceryl cocoate that may be used in cleansing compositions such as body washes, shampoos, liquid hand soap, facial washes, dish detergents and car wash detergents. The alkoxylated derivatives of glyceryl cocoate provide improved multifunctional performance properties including conditioning, viscosity building, emulsification, foaming and skin-feel properties.

BACKGROUND OF THE INVENTION

The development of cleansing products (including, without limitation, liquid hand soaps, body washes, shampoos, bath washes, hair conditioners, liquid dish detergents, car wash detergents, and the like) has long been driven by the challenge of providing a combination of performance properties such as good foaming, good cleansing, good rinsing, enhanced mildness, and improved skin feel. This combination of properties is even more challenging to provide in clear cleansing products, which are highly desired. Often the addition of a component to a cleansing composition formulation may enhance one property to the detriment of another desired property of the composition. For example, a composition may enhance skin conditioning by incorporating emollients at the expense of foaming. Therefore, those in the relevant art have been seeking new formulations to help achieve the balance of desirable performance properties.

Examples of developments in cleansing formulations seeking to balance low irritation, good tactile characteristics, good foaming, and good cleansing include U.S. Pat. No. 4,664,835 to Grollier et al., which describes a washing and cleansing formulation containing a synthetic surfactant and an anionic polymer; U.S. Pat. No. 5,646,100 to Haugk et al., which describes a liquid personal cleansing formulation containing an anionic surfactant, a betaine, and an alkyl polyglycoside; and U.S. Pat. No. 5,310,508 to Subramanyam et al., which describes a personal cleansing composition containing a salt of alcohol ethoxy glyceryl sulfonate ("AGS") and a second synthetic surfactant.

It is well known that a liquid cleansing composition is typically aqueous and comprises one or more mild detersive surfactants and/or soaps. For example, conventional hand cleansers, body washes, shampoos, or liquid soap typically comprise a synthetic detersive and/or fatty acid soap and one or more foam stabilizing, wetting, or emulsifying surfactants.

However, cleansing compositions based on synthetic detergents often impart poor skin feel during and after use, and require additives to improve such tactile aspects of performance. One known emollient for improving skin feel and softness is polyethylene glycol-7 glyceryl cocoate (PEG-7 glyceryl cocoate), which is a polyethylene glycol ether of glyceryl cocoate containing an average of 7 moles of ethylene oxide. PEG-7 glyceryl cocoate is commercially available from a number of sources, such as Croda, Inc., under the trade name Glycerox HE, Cognis Corporation, under the trade name Cetiol HE, and Degussa Care Specialties, under the trade name Tegosoft GC. Although the incorporation of such an emollient may help to improve skin feel in cleansing compositions, it may not contribute to other necessary properties, such as attractive product appearance and viscosity, and may have a negative effect on foaming. Thus, additional components, such as foam builders and viscosity builders, may need to be incorporated into the cleansing compositions, which can lead to an increased cost in producing such compositions. Further, at concentrations higher than about 2% by weight, PEG-7 glyceryl cocoate may be difficult to mix into aqueous systems, especially at ambient temperatures, which may require more elaborate and/or costly mixing procedures to produce the cleansing compositions.

Despite these developments, there remains a need for a cleansing formulation that provides enhanced skin feel, low skin irritation, low skin drying, good cleansing ability, good foaming, and good rinsability characteristics/properties, especially in a clear cleansing product. There also remains a need for a cleansing formulation that utilizes components that are multi-functional, thereby obtaining a desired balance of properties with fewer components, which result in lower costs of production.

SUMMARY OF THE INVENTION

The presently described technology relates to cleansing compositions comprising a water-compatible emollient that comprises an alkoxylated derivative of glyceryl cocoate that incorporates both ethylene oxide and propylene oxide groups in the molecular structure. The water-compatible emollient imparts improved multifunctional performance properties to the cleansing composition, including improved skin-feel characteristics (e.g., skin and/or hair softness and moisturization), viscosity building properties, cleansing, rinsing, and emulsification properties (e.g., improved stability, reduced and uniform droplet size). In a preferred embodiment, the cleansing composition of the present technology is clear.

In one embodiment there is provided a cleansing composition comprising at least one surfactant, at least one emollient comprising a polyethylene glycol/polypropylene glycol derivative of glyceryl cocoate, and water. The cleansing composition may be suitable for use as a liquid hand soap, body wash, or shampoo composition.

Further embodiments of the present technology may additionally incorporate skin conditioners, rheological modifiers, fragrances, colorants, opacifiers, pearlescent agents, herbal extracts, vitamins and the like. Additional embodiments may also be configured to be suitable as shower gels, hair conditioners, dishwashing detergents, or car wash detergents.

While the presently described technology will be described in connection with one or more preferred embodiments, it will be understood by those skilled in the art that it is not limited to those embodiments. On the contrary, the presently described technology includes all alternatives, modifications, and equivalents as may be included within the spirit and scope of the appended claims.

DETAILED DESCRIPTION OF THE INVENTION

The cleansing compositions of the presently described technology comprise at least one primary surfactant, a water-compatible emollient comprising a polyethylene glycol/polypropylene glycol derivative of glyceryl cocoate, and water. More preferably, the cleansing compositions of the presently described technology comprise one or more primary surfactants, one or more secondary surfactants, the water-compatible emollient, and water.

It has been unexpectedly determined that the addition of a nonionic water-compatible emollient, in particular an ethoxylated and propoxylated derivative of glyceryl cocoate, to cleansing compositions provides not only enhanced skin-feel characteristics, but also improved viscosity-building properties. It is also believed that the emollient provides improved emulsification in liquid cleansing products.

The emollient is a polyoxyethylene, polyoxypropylene derivative of glyceryl cocoate preferably containing an average of 6 moles of ethylene oxide and 2 moles of propylene oxide (PEG/PPG-6/2 glyceryl cocoate). The product is made by reacting coconut oil and glycerin, and further alkoxylating with ethylene oxide and propylene oxide to achieve the glyceryl cocoate derivative having an average of 6 moles of ethylene oxide and 2 moles of propylene oxide. A commercially available example of PEG/PPG-6/2 glyceryl cocoate may be obtained from Stepan Company, Northfield, Ill. under the trade name STEPAN® 745 GC.

Ethoxylated derivatives of glyceryl cocoate, such as PEG-7 glyceryl cocoate, have been used in personal cleansing compositions as emollients and skin conditioning agents. However, such derivatives only contain an ethylene oxide component. While not wishing to be bound by any particular theory, it is believed that the incorporation of propylene oxide groups in the PEG/PPG-6/2 glyceryl cocoate derivative used herein provides unexpectedly improved viscosity-building properties, enhanced skin-feel characteristics and improved emulsification in liquid cleansing products.

Preferably, the PEG/PPG-6/2 glyceryl cocoate emollient comprises from about 0.1% to about 10%, alternatively, about 0.15% to about 9%, alternatively about 0.2% to about 8%, alternatively about 0.25% to about 7%, alternatively about 0.3% to about 7%, alternatively about 0.4% to about 7%, by weight of the total weight of a finished personal cleansing composition The emollient is conveniently incorporated into a personal cleansing composition by mixing the emollient into the surfactant system used in the personal cleansing composition. The emollient can be cold-mixed (at ambient temperatures), although slight heating, for example up to about 40° C., can accelerate the mixing process. Even at concentrations of up to 10% by weight, the PEG/PPG-6/2 glyceryl cocoate emollient is clear in surfactant systems, making the emollient particularly suitable for clear cleansing products. However, the emollient is not limited to clear cleansing products and may also be used in cleansing products that are translucent, opaque or have a pearlescent appearance. The emollient is also water-compatible. At concentrations up to about 2% the emollient is clear in water, and at higher concentrations the emollient is dispersible in water.

The surfactant system used in the cleansing compositions of the present technology comprises at least one primary surfactant. Preferably, the surfactant system comprises at least one primary surfactant and at least one secondary surfactant. In some embodiments of the present technology, the surfactant system comprises one or more primary surfactants and one or more secondary surfactants.

The primary surfactant or surfactants may be a suitable anionic, nonionic, cationic, amphoteric, or zwitterionic surfactant, and preferably comprises from about 0.1% to about 70% by weight of the total cleansing composition, more preferably, from about 5% to about 60% by weight of the total cleansing composition.

Suitable anionic surfactants, include, without limitation: sulfonated alkyl benzene, sulfonated methyl esters, sulfonated alpha olefin, paraffin sulfonate, alkyl sulfate, alkyl alkoxy sulfate, alkyl alkoxy carboxylate, alkyl phosphate, alkyl alkoxy phosphate, alkyl sulfonate, alkyl alkoxylated sulfate, acyl lactylate, alkyl isethionate, salts thereof, and combinations thereof. Further examples can be found in "Surface Active Agents and Detergents" (Vol. I and II by Schwartz, Perry and Berch).

Suitable nonionic surfactants include, without limitation: fatty acid amide, ethoxylated fatty acid amide, alkyl alcohol, alkyl alcohol ethoxylate, alkyl phenol ethoxylate, propylene glycol esters, polyglycerol esters, ethylene glycol esters, ethoxylated glycol esters, polypropylene glycol esters, alkylpolyglycoside, alkyl glucamide, and combinations thereof. More examples are generally disclosed in U.S. Pat. No. 3,929,678 to Laughlin et al., issued on Dec. 30, 1975 at column 13, line 14 through column 16, line 6, and those described in U.S. Pat. No. 4,199,483 (Jones), both incorporated herein by reference.

Cationic surfactants and cationic polymers may include, without limitation: alkyl dimethylammonium halogenide, quaternized cellulose, quaternized quar gum, esterquat, amidoquat, and stearylammidopropyl dimethyl amine quat. Other cationic surfactants useful herein are also described in U.S. Pat. No. 4,228,044 to Cambre, issued Oct. 14, 1980, incorporated herein by reference. Suitable commercially available primary surfactants include, without limitation, the STEOL® series, the ALPHA-STEP® series, including ALPHA-STEP® PC-48 (sodium methyl 2-sulfolaurate and disodium 2-sulfolaurate), BIO-TERGE® AS-40, and STEPANOL® AM-V surfactants manufactured by Stepan Company, Northfield, Ill.

Suitable zwitterionic co-surfactants include, without limitation, betaine surfactants, such as alkyl betaine and alkyl amidobetaine, and sultaine surfactants, such as alkyl sultaine and alkylamido sultaine. Additional zwitterionic surfactants are exemplified by those which can be broadly described as derivatives of aliphatic quaternary, ammonium, phosphonium and sulfonium compounds, and betaines. Further detailed descriptions of such surfactants are disclosed in U.S. Pat. No. 5,705,147 (Shapiro et al.) incorporated herein by reference Amphoteric surfactants suitable for use in the compositions described herein include derivatives of aliphatic secondary and tertiary amines. Further detailed description of such amphoteric surfactants may be found in U.S. Pat. No. 5,705,147 to Shapiro et al., incorporated herein by reference.

Suitable secondary surfactants include for example, anionic surfactants, betaines, amine oxide, fatty acid amide, ethoxylated fatty acid amide and acyl lactylate. The secondary surfactant or surfactants may comprise from about 0.1% to about 50% by weight of the total cleansing composition, more preferably from about 1% to about 15% by weight of the total cleansing composition. Suitable commercially available secondary surfactants include, without limitation, the AMPHOSOL® series (betaines and sultaines), the ALPHA-STEP® series, including ALPHA-STEP® PC-48 (sodium methyl 2-sulfolaurate and disodium 2-sulfolaurate), and NINOL® COMF surfactants manufactured by Stepan Company, Northfield, Ill., or other surfactants disclosed and discussed below in the Examples.

The cleanser compositions described herein are preferably in the form of liquids or creams in which water is the principal diluent. Alternatively, although less preferred, other solvents such as alcohols may be utilized. The level of water in a liquid cleansing composition is preferably from about 20% to about 99% by weight.

Optional Ingredients:

The formulations of the presently described technology may be used alone as a liquid cleansing composition, preferably as a body wash, hand wash, facial cleanser, shampoo or the like. Alternatively, other optional ingredients may be added to make the present compositions more preferable for a variety of different uses such as a pumpable liquid hand cleanser, 2-in-1 shampoo, dish soap, gel body wash, bath soap, or the like.

For example, thickeners may be added if necessary to achieve a desired viscosity for a particular cleansing composition. Such thickening agents may include, for example, polymeric thickening agents, such as esterquat, amidoquat, stearylammidopropyl dimethyl amine quat, cellulosic polymers, and acrylic polymers and copolymers. Alternatively, the cleansing products may be thickened by using polymeric additives that hydrate, swell or molecularly associate to provide body, such as, for example, hydroxypropyl guar gum. Other suitable thickening agents may include, without limitation, those listed in the Glossary and Chapters 3, 4, 12 and 13 of the *Handbook of Water-Soluble Gums and Resins*, Robert L. Davidson, McGraw-Hill Book Co., New York, N.Y. 1980.

Fatty acid soaps, builders, and additional surfactants may be added to aid in cleansing ability. Emollients (including, without limitation, vegetable oils, mineral oils, silicone oils, petrolatum, polyglycerol methyl esters, and esters), skin conditioning agents (such as glycerine and free fatty acid), vitamins and herbal extracts may be added to further improve conditioning performance. Fragrances, dyes, opacifying agents, and pearlescent agents may also be added to further enhance the appearance and smell of the finished formulation. Suitable preservatives such as benzyl alcohol, methyl paraben, propyl paraben, imidazolidinyl urea and DMDM hydantoin may be utilized. Antibacterial agents such as quaternary ammonium compounds may also be utilized. Furthermore, a dimethyl polysiloxane may be utilized to enhance skin feel and conditioning properties to hair.

The compositions and the methods of producing such compositions herein may be formulated and carried out such that they will have a pH of between about 4.0 to about 8.5, preferably, between about 5.0 to about 7.0. Techniques for controlling pH at recommended usage levels include the use of buffers, alkali, acids, etc., and are well known to those skilled in the art. Optional pH adjusting agents can include, but are not limited to citric acid, succinic acid, phosphoric acid, sodium hydroxide, sodium carbonate, and the like.

EXAMPLES

The following examples describe some of the preferred embodiments of the present technology without limiting the technology thereto. Other embodiments include, but are not limited to, those described in the above written description, including additional or alternative components, alternative concentrations, and additional or alternative properties and uses.

TABLE A

| Composition Trade Names & Abbreviations | |
|---|---|
| BIO-TERGE® AS-40 CG-P | sodium $C_{14}$-$C_{16}$ olefin sulfonate |
| ALPHA-STEP® PC-48 | average 6:1 ratio of sodium sulfonated methyl $C_{12}$-$C_{18}$ ester (and) disodium sulfonated $C_{12}$-$C_{18}$ fatty acid |
| STEOL® CA-130 | ammonium laureth sulfate with 1 mole ethylene oxide per mole of alcohol |
| STEOL® CA-230 | ammonium laureth sulfate with 2 moles ethylene oxide per mole of alcohol |
| STEOL® CS-130 | sodium salt of $C_{12}$-$C_{14}$ alkyl ethoxy sulfate with 1 mole ethylene oxide per mole of alcohol |
| STEOL® CS-230 | sodium salt of $C_{12}$-$C_{14}$ alkyl ethoxy sulfate with 2 moles ethylene oxide per mole of alcohol |
| AMPHOSOL® HCG | cocamidopropyl betaine |
| AMPHOSOL® HCA | cocamidopropyl betaine |
| NINOL COMF | cocamide monoethanol amine (MEA) |
| STEPANOL® AM-V | ammonium lauryl sulfate |
| STEPAN® 745 GC | alkoxylated derivative of glyceryl cocoate having an average of 6 moles ethylene oxide and 2 moles propylene oxide |

Examples 1 and 2

Examples 1 and 2 are formulations of a sodium-based surfactant system to which the water compatible emollient (STEPAN® 745 GC) has been added in increments of 1% by weight ranging from 1% to 10% by weight.

TABLE B

Examples 1 and 2 (sodium-based surfactant formulations)

| | Example 1 | | Example 2 | |
|---|---|---|---|---|
| Ingredient | % active | % wt. | % active | % wt. |
| STEOL® CS-230 | 12 | 46.6 | 12 | 46.6 |
| AMPHOSOL® HCA | 3 | 10 | | |
| AMPHOSOL® HCG | | | 3 | 10 |
| STEPAN® 745 GC | 1.0-10.0 | 1.0-10.0 | 1.0-10.0 | 1.0-10.0 |
| D.I. Water | | Q.S. to 100 | | Q.S. to 100 |

Procedure:

1. Charge D.I. water and surfactants. Mix well.
2. Add STEPAN® 745 GC. Mix until clear.

STEPAN® 745 GC can be mixed cold (at ambient temperature) but the mixing can take a long time. Light heat (e.g., up to 40° C.) can accelerate the mixing process. At concentrations up to 10% by weight, the STEPAN® 745 GC emollient is clear in the surfactant system.

The viscosity-building properties of the Example 1 and 2 formulations were evaluated at each concentration of the STEPAN® 745 GC emollient. Viscosity was measured using a Brookfield LT, spindle #4 at 12 rpm for 60 seconds. The results are shown in Table C and graphically in FIG. 1.

TABLE C

Viscosity Results for Examples 1 and 2

| 745 GC conc. % wt. | Example 1 CS-230/HCA surfactants Viscosity (cps) | Example 2 CS-230/HCG surfactants Viscosity (cps) |
|---|---|---|
| 1 | 50 | 10 |
| 2 | 50 | 20 |
| 3 | 150 | 50 |
| 4 | 350 | 150 |
| 5 | 750 | 230 |
| 6 | 1,450 | 510 |
| 8 | 3,100 | 1,520 |
| 10 | 3,500 | 2,480 |

Figure 1:
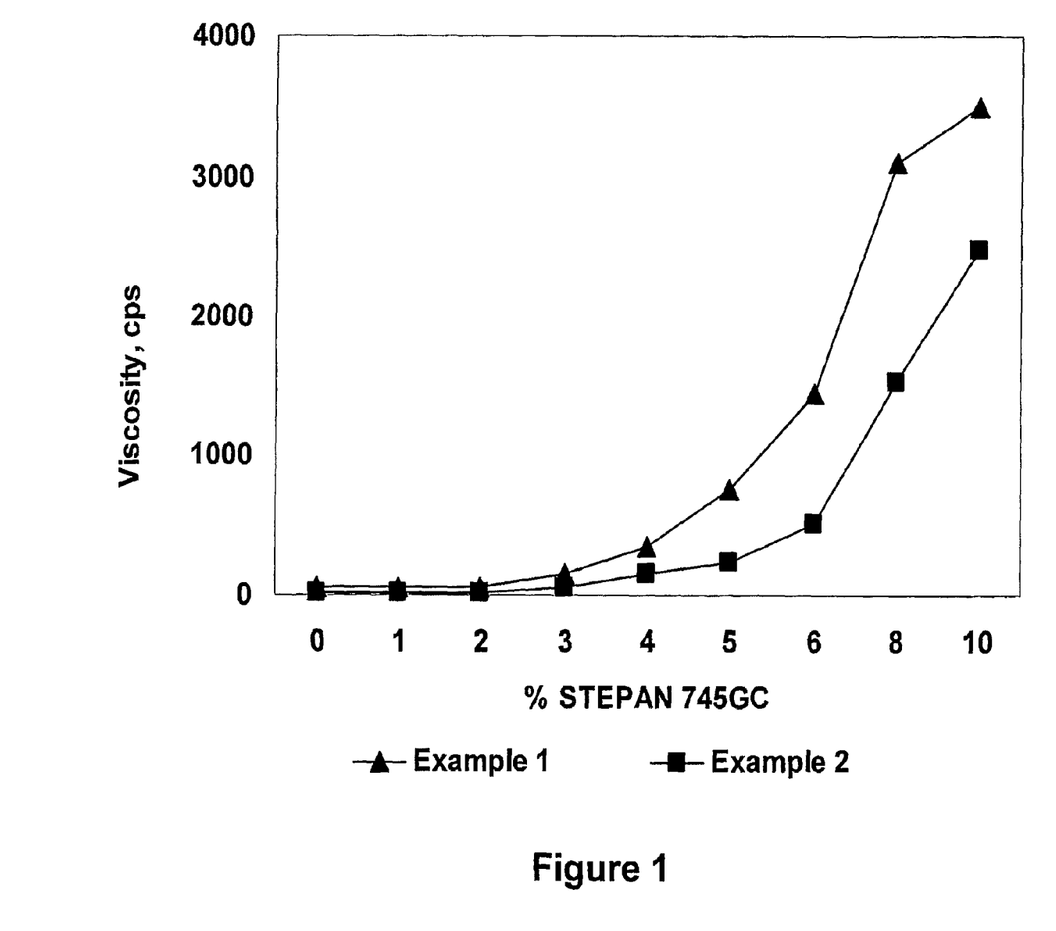
FIG. 1 is a graph illustrating the viscosity-building properties of the alkoxylated derivative of glyceryl cocoate in sodium-based surfactant systems.

As can be seen from Examples 1 and 2 and the results shown in Table C and FIG. 1, the STEPAN® 745 GC component can be cold blended with sodium-based surfactant systems to yield clear solutions and provide excellent viscosity-building properties.

Example 3

Comparative

The surfactant system from Example 1 (GS-230/HCA) was prepared and used to evaluate the viscosity-building properties of two competitive emollients. Both products are PEG-7 glyceryl cocoates containing only ethylene oxide (no propylene oxide) components. The procedure was the same as that used for Examples 1 and 2 and each emollient product was added to the surfactant system in increments of 1% by weight. Both products were difficult to mix into the surfactant system at concentrations higher than 2%, and the products stuck to the mixing blade. This did not occur with the STEPAN® 745 GC product used in Example 1.

The viscosity-building properties of the competitive products were evaluated at each concentration. Viscosity was measured using a Brookfield LT spindle #4 at 12 rpm for 60 seconds. The results are shown below in Table D, along with the results from Example 1, for comparison purposes, and also shown graphically in FIG. 2.

TABLE D

Viscosity, Results for Comparative Example 3 and Example 1

| | Example 3 (comparative) Viscosity (cps) | | Example 1 |
|---|---|---|---|
| % conc. | Competitive Product 1 | Competitive Product 2 | Viscosity (cps) |
| 1 | 0 | 50 | 50 |
| 2 | 0 | 50 | 50 |
| 3 | 50 | 50 | 150 |
| 4 | 50 | 100 | 350 |
| 5 | 100 | 150 | 750 |
| 6 | 100 | 200 | 1,450 |
| 8 | 350 | 450 | 3,100 |
| 10 | 750 | 1,000 | 3,500 |

Figure 2:
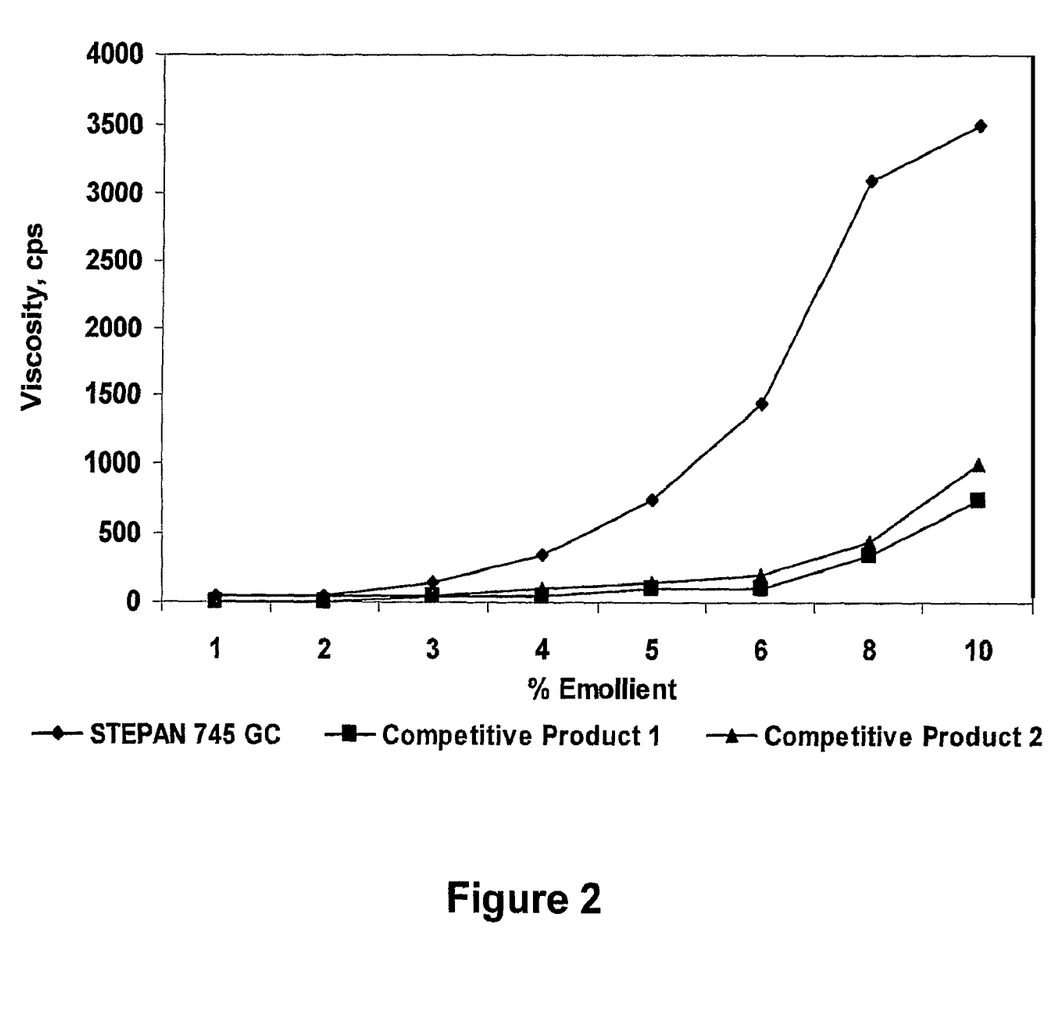
FIG. 2 is a graph comparing the viscosity-building properties of the alkoxylated derivative of glyceryl cocoate of the present technology with competitive PEG-7 glyceryl cocoate emollients.

As can be seen from the above results and FIG. 2, the use of the PEG/PPG-6/2 glyceryl cocoate emollient (STEPAN® 745 GC) in the Example 1 formulation provides significantly better viscosity-building properties than the competitive PEG-7 glyceryl cocoate emollients.

Example 4

Figure 3:
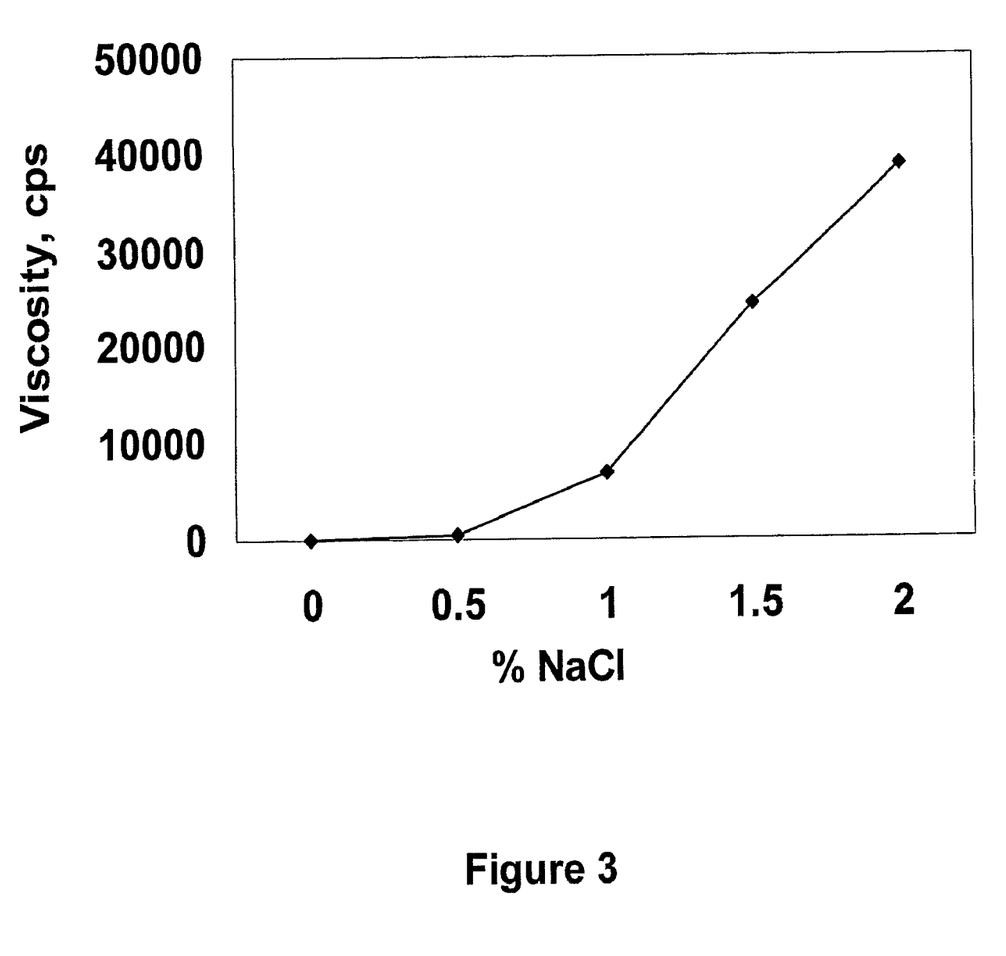
FIG. 3 is a graph illustrating the effect of different salt concentrations on the viscosity-building properties of the alkoxylated derivative of glyceryl cocoate of the present technology.

In accordance with the procedure used for Examples 1 and 2, the STEPAN® 745 GC emollient was added to the Example 1 surfactant system at a concentration of 2% by weight. Different concentrations of sodium chloride (NaCl) salt ranging from 0% to 2% were added to the surfactant system to determine the effect of salt concentration on the viscosity profile of the surfactant system at 2% emollient concentration. The results are shown graphically in FIG. 3. As can be seen from the FIG. 3 graph, small amounts of sodium chloride (e.g., 1-2%) added to the formulation can result in a significant increase in the viscosity of the formulation.

Examples 5 and 6

Examples 5 and 6 are formulations of an ammonium-based surfactant system to which the PEG/PPG-6/2 glyceryl cocoate (STEPAN® 745 GC) emollient has been added in increments of 1% by weight from 1% to 8% by weight.

TABLE E

Examples 5 and 6 (ammonium-based surfactant formulations)

| | Example 5 | | Example 6 | |
|---|---|---|---|---|
| Ingredient | % active | % wt. | % active | % wt. |
| STEOL ® CA-230 | 12 | 47.5 | 12 | 47.5 |
| AMPHOSOL ® HCG | 3 | 10.0 | | |
| AMPHOSOL ® HCA | | | 3 | 10 |
| STEPAN ® 745 GC | 1.0-8.0 | 1.0-8.0 | 1.0-8.0 | 1.0-8.0 |
| D.I. water | | Q.S. to 100 | | Q.S. to 100 |

Figure 4:
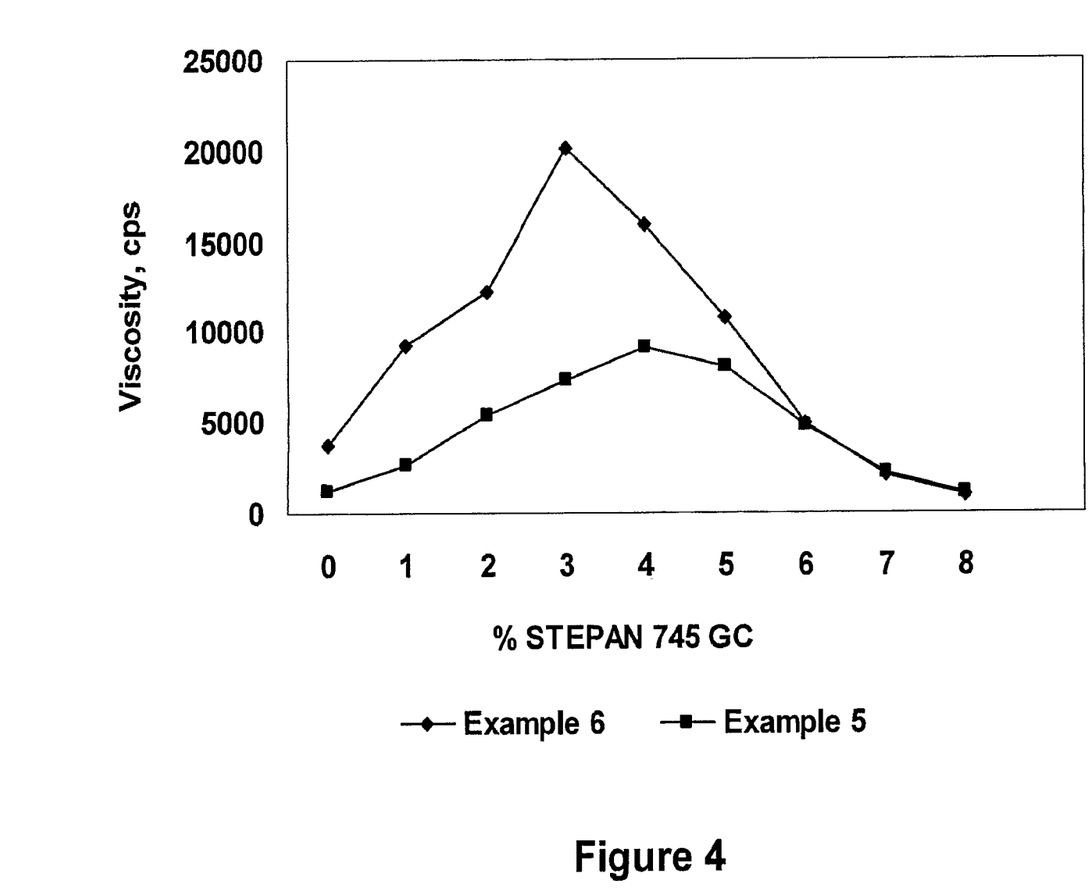
FIG. 4 is a graph illustrating the viscosity-building properties of the alkoxylated derivative of glyceryl cocoate in ammonium-based surfactant systems.

The mixing procedure used was the same as that used for Examples 1 and 2. At concentrations up to 8% by weight, the STEPAN® 745 GC emollient is clear in the ammonium-based surfactant system. The viscosity-building properties of the Example 5 and 6 formulations were evaluated at each concentration of the STEPAN® 745 GC emollient. Viscosity was measured using a Brookfield LT, spindle #4 at 12 rpm for 60 seconds. The results are shown graphically in FIG. 4.

Examples 7 and 8

Shake Foam Test Formulations

For Example 7, a surfactant system identical to the STEOL® CS-230/AMPHOSOL® HCA surfactant system used in Example 1 was used as a base formulation, and the STEPAN® 745 GC emollient was added to the base formulation in 1% by weight increments ranging from 1% to 10% by weight. For Example 8, a surfactant system identical to the STEOL® CA-230/AMPHOSOL® HCA surfactant system used in Example 6 was used as a base formulation, and the STEPAN® 745 GC emollient was added to the base formulation in 1% by weight increments ranging from 1% to 10% by weight.

A standard shake foam test using 2% by weight castor oil was performed on each base surfactant formulation and on each formulation containing each 1% increment of the STEPAN® 745 GC emollient.

The foaming profiles of the Example 7 and 8 formulations were evaluated at each concentration of the STEPAN® 745 GC emollient and compared to the base formulation. The results of the foaming test are graphically illustrated in FIG. 5 for the Example 7 formulations, and in FIG. 6 for the Example 8 formulations.

Figure 5:
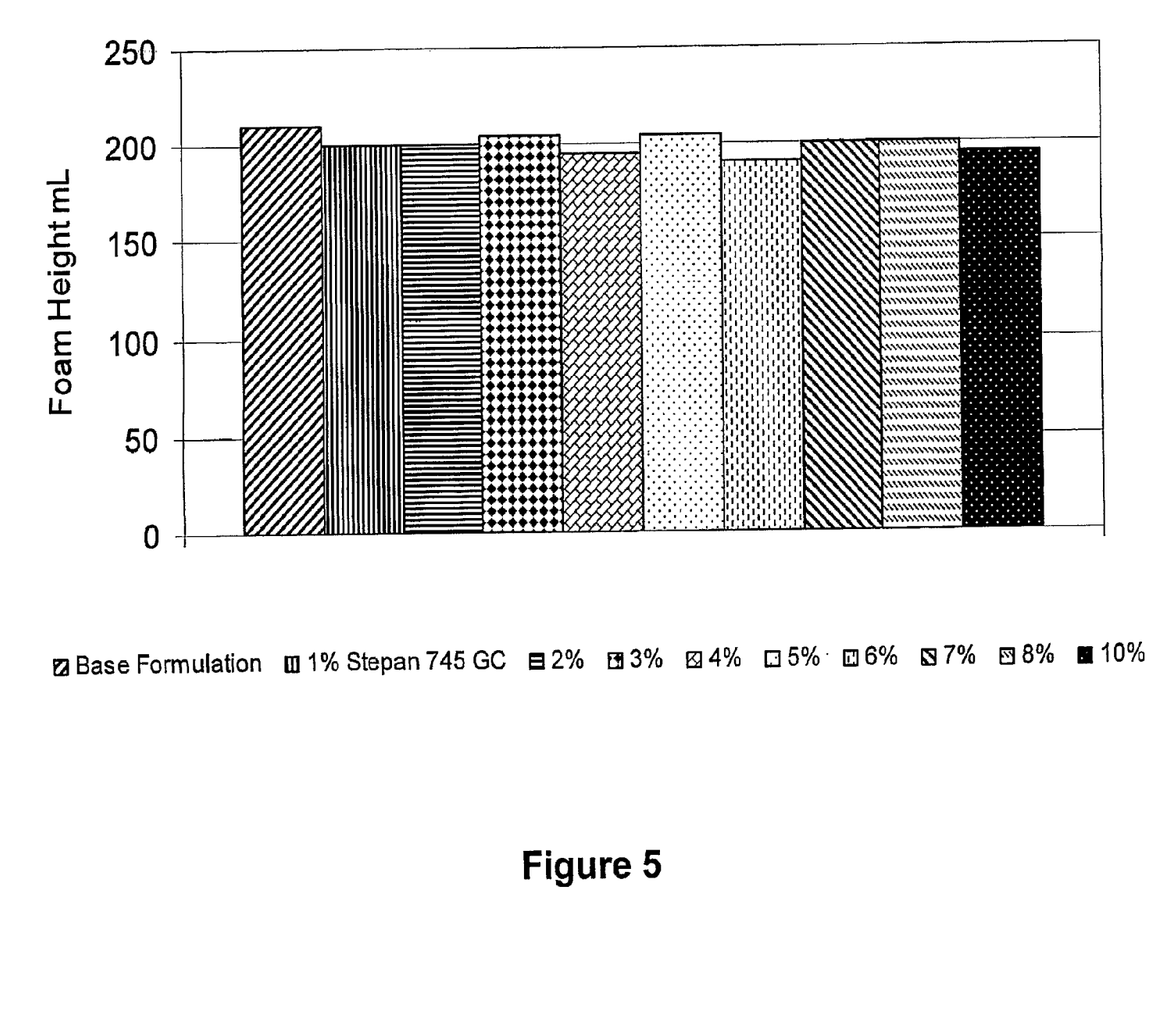
FIG. 5 is a graph illustrating the foaming profile of the alkoxylated derivative of glyceryl cocoate in a sodium-based surfactant system with 2% castor oil added.
Figure 6:
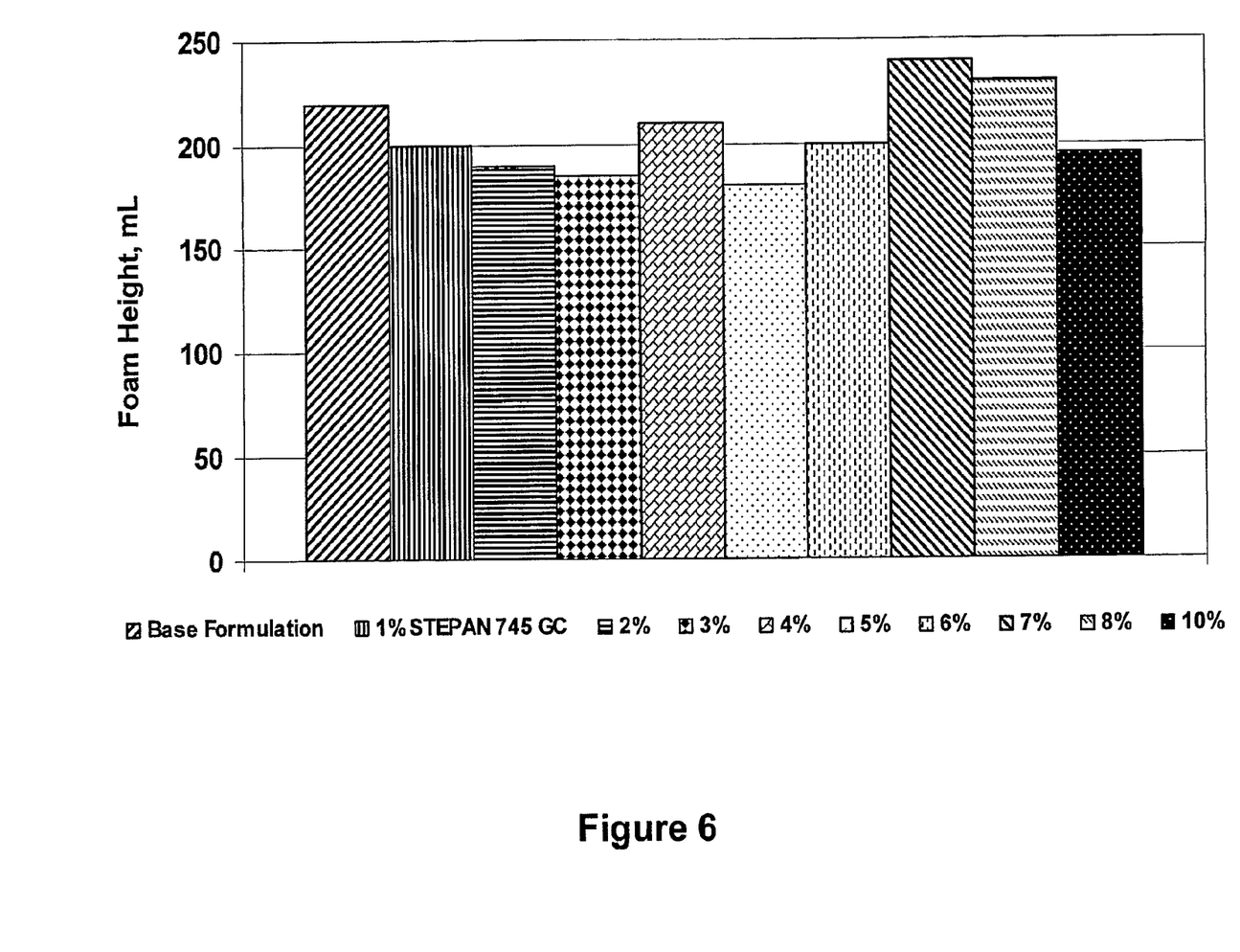
FIG. 6 is a graph illustrating the foaming profile of the alkoxylated derivative of glyceryl cocoate in an ammonium-based surfactant system with 2% castor oil added.

As can be seen from the FIG. 5 and FIG. 6 graphs, the addition of the STEPAN® 745 GC emollient, in concentrations ranging from 1% to 10% by weight, does not detrimentally effect foaming performance of the cleansing composition.

Example 9

Control Formulation

Example 9 is a control formulation, for testing comparison, indicated in weight percent active.

| Ingredient | Example 9 Wt. % Active |
| --- | --- |
| STEOL ® CS-230 | 12.0 |
| AMPHOSOL ® HCG | 3.0 |
| WATER | 85.0 |

Example 10

Example 10 is a formulation of a sodium-based surfactant system to which the STEPAN® 745 GC emollient has been added in an amount of 8% by weight. The formulation is set forth in Table F.

TABLE F

| Example 10 (sodium-based surfactant formulation) | |
| --- | --- |
| Ingredient | Example 10 Wt. % Active |
| STEOL ® CS-230 | 12.0 |
| AMPHOSOL ® HCG | 3.0 |
| STEPAN ® 745 GC | 8.0 |
| WATER | 77.0 |

Example 11

Comparative

Example 11 is a formulation of the same sodium-based surfactant system used in control Example 9 and Example 10, except that 8% by weight of a PEG-7 glyceryl cocoate competitive emollient was added to the formulation. The formulation is set forth in Table G.

TABLE G

| Example 11 (Comparative) | |
| --- | --- |
| Ingredient | Example 11 Wt. % Active |
| STEOL ® CS-230 | 12.0 |
| AMPHOSOL ® HCG | 3.0 |
| PEG-7 glyceryl cocoate | 8.0 |
| WATER | 77.0 |

Examples 9, 10 and 11 were prepared in de-ionized water. The final pH of each composition was adjusted to between 5-6 with either sodium hydroxide (50%) or citric acid (50%). Foaming and skin-feel evaluation for all three examples was carried out using an in-vivo human expert panel test. Example 10, in accordance with the present technology, was compared to a 12% anionic, 3% betaine control formulation (Example 9) containing sodium laureth sulfate and cocamidopropyl betaine at a 4:1 active ratio (STEOL® CS-230/AMPHOSOL® HCG), and also to the competitive formulation of Example 11, containing 8% by weight of a commercially available PEG-7 glyceryl cocoate emollient.

At least six panelists with different skin types (dry, normal, and moist) were chosen for each test. The skin type of the panelist was determined using a NOVA meter. A NOVA reading less than 100 represents dry skin, 110-130, normal skin and 130 or above, moist skin. The panelists were asked to assess the performance of the experimental product (Example 10) and the control (Example 9) or the commercial product (Example 11) in a blind test using a 1 to 5 rating scale, with 1 being the worst and 5 being the best. Panelists were not told which samples were the experimental formulation, and which samples were the control or commercial product.

Panelists were asked to assess the following characteristics during and after the washing procedure: foam volume, skin softness, skin dryness, and tackiness during drying. To identify tackiness during drying, the panelists were instructed that some products may impart a sticky/tacky feel on the skin during the transition from a wet to a dry stage. Tackiness can be assessed by touching the fingers of the same hand together or by force required to separate fingers. To identify skin tightness when dry, the panelists were instructed that some products may leave the skin feeling tight or stretched after the skin is completely dry. The panelists were instructed that this property should not be evaluated until the panelist is sure that the hands are completely dry. Similarly, skin dryness was evaluated once the hands were completely dry.

To identify skin softness, the panelists were instructed to characterize how soft and smooth the skin feels to the touch. A product can often leave the skin feeling dry, but smooth. The positive extreme would be a smooth velvety feel (ranking of 5 on a 1-5 scale), and the opposite would be a rough feeling skin with some grittiness (ranking of 1 on a 1-5 scale). All samples were coded in order to get a fair comparison between the experimental and control products.

Human Panel Test Method
1. Panelists were asked to pre-wash their hands with 15% active sodium lauryl sulfate solution to remove residue from the skin and establish the baseline before evaluating of experimental body washes.
2. Hand washing tests were conducted using luke-warm (95° F. and 105° F.) running tap water.
3. Using a syringe, 1 ml of the test product was dispensed to the panelist's wet palm.
4. The panelists were asked to wash their hands by gently rubbing them together for 30 seconds followed by rinsing under running tap water for 15 seconds.
5. The panelists were asked to rank the product for wet properties using a 1-5 scale.
6. The hands were dried using paper towel, and then evaluated for wet to dry stage transition properties.
7. Skin feel evaluation was done at ambient temperature (~25° C.).

Figure 7:
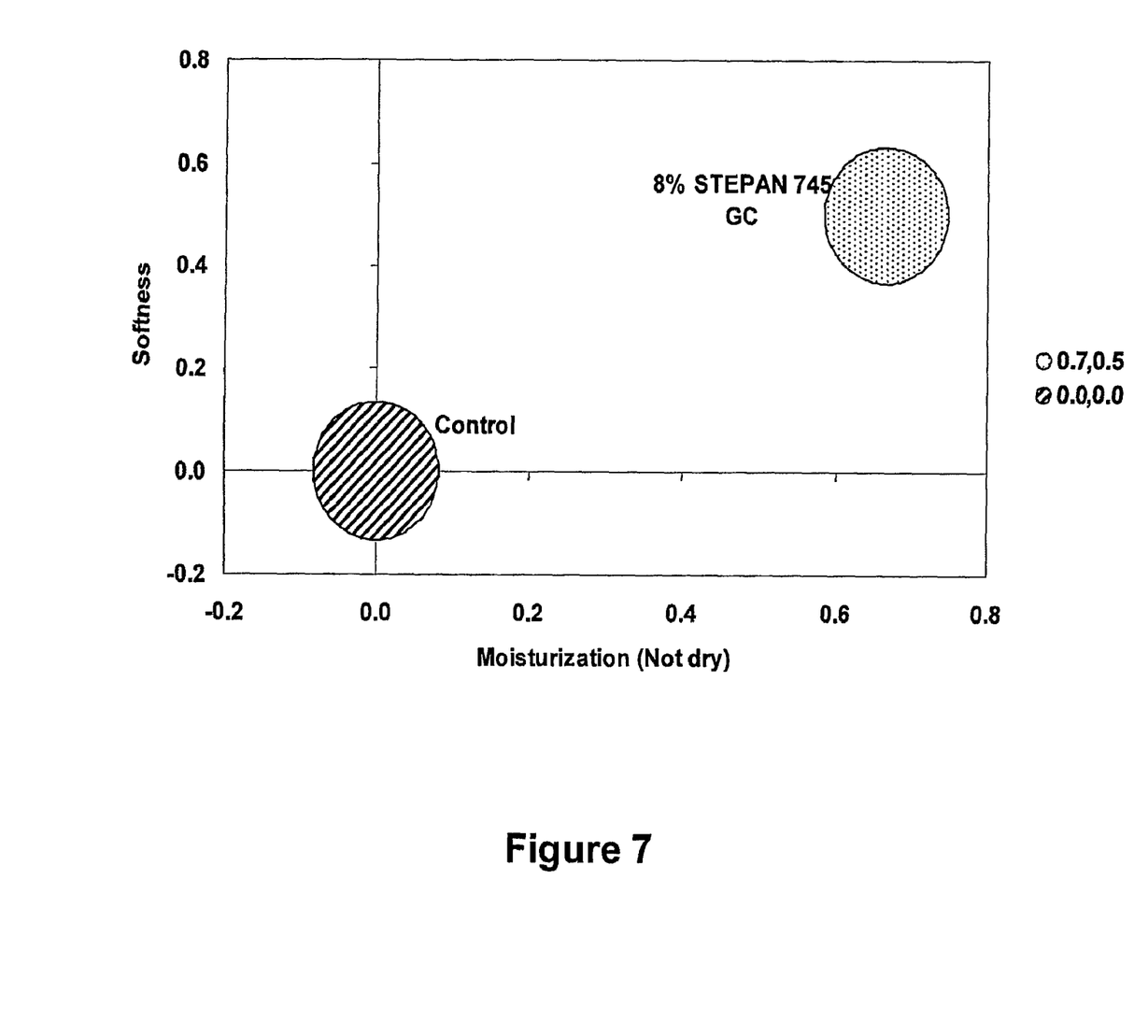
FIG. 7 is a bubble chart comparing the skin-feel properties of a composition in accordance with the present technology with the skin-feel properties of a control composition.

The average response for the panelists, for the experimental formulation, is subtracted from the average response for the control formulation. A positive score indicates that the experimental formulation outperformed the control. The results for the comparison of the experimental formulation of Example 10 with the control formulation of Example 9 are shown in the bubble graph of FIG. 7. As illustrated in FIG. 7, the formulation of Example 10, in accordance with the present technology, gives improved skin-feel characteristics compared to the Example 9 control formulation.

Figure 8:
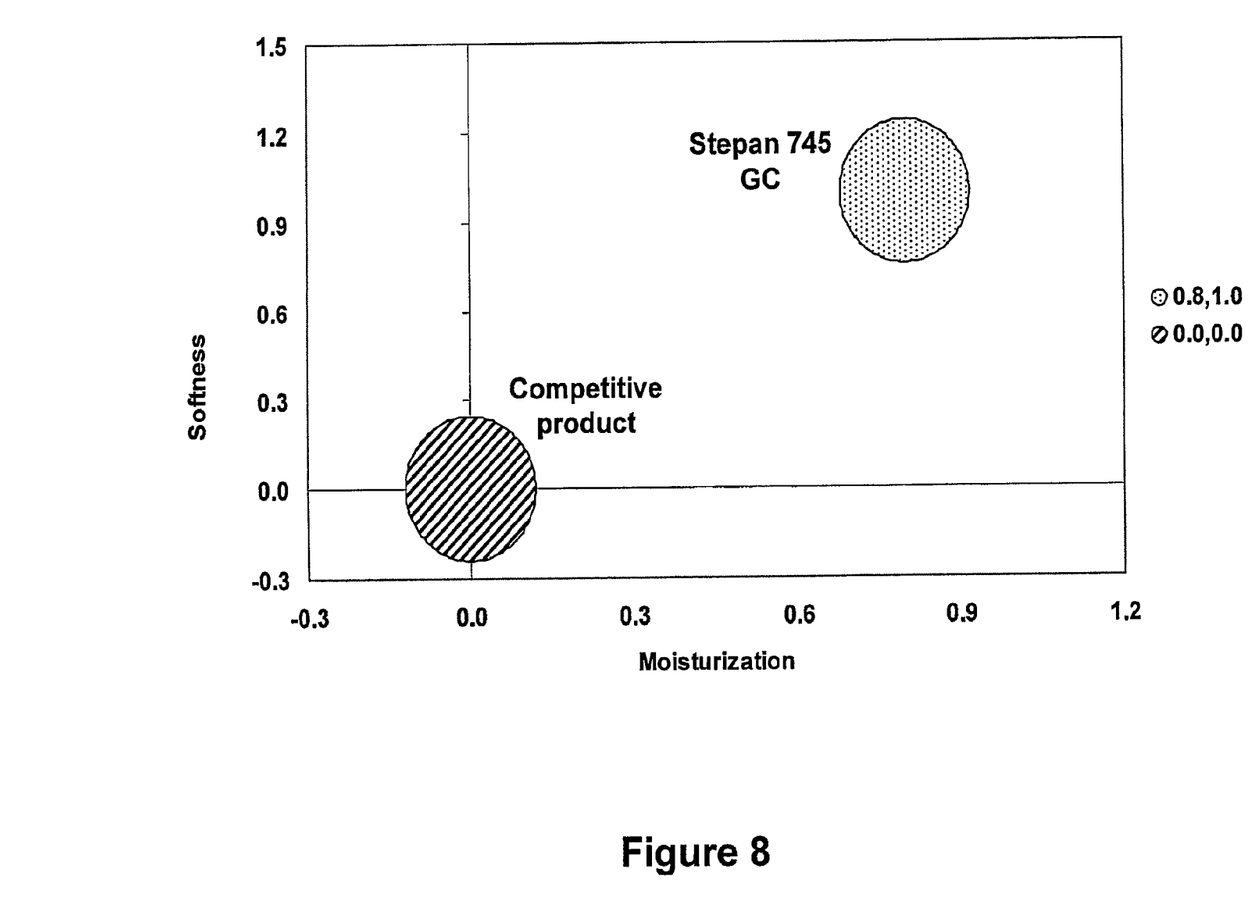
FIG. 8 is a bubble chart comparing the skin-feel properties of a composition in accordance with the present technology with the skin-feel properties of a competitive composition.

A similar comparison was made between the experimental formulation of Example 10 and the competitive formulation of Example 11. A positive score indicates that the experimental formulation out-performed the competitive formulation. The results for the comparison of the Example 10 formulation with the competitive formulation of Example 11 are shown in the bubble graph of FIG. 8. As illustrated in FIG. 8, the formulation of Example 10, in accordance with the present technology, gives improved skin-feel characteristics compared to the competitive formulation of Example 11.

Yet another feature of the polyethylene glycol/polypropylene glycol derivative of glyceryl cocoate water compatible emollient (STEPAN® 745GC) is the improved emulsification properties in liquid cleansing products. Table H lists examples of two screening formulations, in which Sample A contains the described inventive technology, while Sample B contains a commercially available competitive product (PEG-7 Glycerol Cocoate available from Croda).

TABLE H

Examples A and B (emulsification properties)

| Ingredient % be weight | Example A With 745 CG | Example B Glycerox HE (Croda) |
|---|---|---|
| Water, D.I. | 88 | 88 |
| Stepan IPM* | 10 | 10 |
| Stepan 745 CG | 2 | None |
| Glycerox HE | None | 2 |

*Stepan IPM = isopropyl myristate

Procedure:

1. Charge D.I. water
2. Add 745 CG or Glycerox HE. Mix well.
3. Add IPM and mix with good agitation for 20 minutes.
4. Evaluate.

Observations:

In one hour after the agitation was stopped, both formulations showed signs of separation. However the formulation with Glycerox HE turned transparent with a significant amount of oils floating on the surface, while the formulation with 745 GC maintained a milky white appearance, indicative of emulsified oil droplets.

As can be noted from the above results, the formulation containing the 745 GC water compatible emollient of the presently described technology demonstrates improved emulsification properties over the competitive product.

The formulations in accordance with the present technology in the above examples may be used alone as a liquid cleansing composition, for example, as a body wash, hand wash or shampoo. Alternatively, other optional ingredients may be added as desired to configure the cleansing compositions as, for example, 2-in-1 shampoos, facial cleansers, liquid soaps, dish detergents or car wash detergents. Illustrative formulations for a clear body wash, a facial cleanser, and a conditioning shampoo in accordance with the presently described technology are indicated in Examples 12, 13 and 14.

Example 12

Clear Body Wash

| Phase | Trade Name/Supplier Name | % by Weight |
|---|---|---|
| 1 | Deionized Water | Q.S. to 100.0 |
| 2 | STEOL ® CS-130 | 55.0 |
|  | AMPHOSOL ® HCA | 10.0 |
|  | ALPHA-STEP ® PC-48 | 5.0 |
|  | STEPAN ® 745 GC | 8.0 |
| 3 | Vitamin E Acetate (Roche) Tocopheryl Acetate | 0.1 |
|  | Vitamin A Palmitate (Roche) Retinyl Palmitate | 0.1 |
|  | Versene 100 (Dow Chemical) Tetrasodium EDTA | 0.2 |
| 4 | Preservative, Dye, Fragrance | Q.S. |
|  | Citric Acid (50% aq. Solution) | Q.S. |
|  | Sodium Chloride | Q.S. |

Procedure for the manufacture of Example 12:

1. In a suitable vessel equipped with agitation capabilities, charge Phase 1.
2. Add ingredients of Phase 2 and Phase 3 while continuing mixing.
3. Adjust pH and viscosity with ingredients in Phase 4, if necessary.

Physical Properties:

| Appearance | Clear viscous liquid |
|---|---|
| pH, as is | 5.5-6.0 |
| Viscosity at 25° C., cps | 3,000-5,000 cps |

Example 13

Facial Cleanser

| Phase | Trade Name/Supplier Name | % by Weight |
|---|---|---|
| 1 | Deionized Water | Q.S. |
| 2 | BIO-TERGE ® AS-40 CG-P | 25.0 |
|  | ALPHA-STEP ® PC-48 | 8.5 |
|  | STEPAN ® 745 GC | 6.0 |
|  | Glycerin | 0.8 |
|  | AMPHOSOL ® HCA | 11.6 |
| 3 | NINOL ® COMF | 2.0 |
| 4 | Glydant (Lonza) DMDM Hydantoin | 0.25 |
| 5 | Peptein CAA (Leiner Davis) Collagen Amino Acids | 0.2 |
|  | Fragrance, Dye | Q.S. |
|  | Citric Acid (50%) | Q.S. |
|  | Sodium Chloride | Q.S. |

Procedure for the manufacture of Example 13:

1. In a vessel equipped with heating and agitation capabilities, add Phase 1.
2. Add ingredients of Phase 2.
3. Heat to 60-65° C.
4. Add Phase 3. Mix until well dissolved.
5. Cool to 40° C. Add Phase 4.
6. Cool to ambient temperature. Add Phase 5.
7. Adjust pH and viscosity with ingredients of Phase 5, if necessary.

-continued

Physical Properties:

| Appearance at 25° C. | Clear viscous liquid |
|---|---|
| pH | 5.0-6.0 |
| Viscosity at 25° C., Brookfield LV 4 at 12 rpm | 1,500-2,500 cps |

Example 14

Clear Conditioning Shampoo

| Phase | Trade Name/Supplier Name | % by Weight |
|---|---|---|
| 1 | Deionized Water | Q.S. to 100.0 |
| 2 | Versene NA (Dow Chemical) Disodium EDTA | 0.1 |
|  | STEPANOL ® AMV | 25.0 |
|  | STEOL ® CA-230 | 18.0 |
|  | AMPHOSOL ® HCG | 3.6 |
|  | STEFAN ® 745 GC | 3.0 |
| 3 | NINOL ® COMF | 2.0 |
| 4 | Glydant (Lonza) DMDM Hydantoin | 0.25 |
| 5 | DL-Panthenol (Roche) Panthenol | 0.25 |
|  | Fragrance | Q.S. |
|  | Citric Acid (50%) | Q.S. |
|  | Sodium Chloride | Q.S. |

Procedure for the manufacture of Example 14:

1. In a vessel equipped with heating and agitation capabilities, add Phase 1.
2. Add ingredients of Phase 2.
3. Heat to 60-65° C.
4. Add Phase 3. Mix until well dissolved
5. Cool to 40° C. Add Phase 4.
6. Cool to ambient temperature. Add Phase 5.
7. Adjust pH and viscosity with ingredients of Phase 5, if necessary.

Physical Properties:

| Appearance | Clear viscous liquid |
|---|---|
| pH | 5.5-6.0 |
| Viscosity at 25° C., RV 6 at 20 rpm, cps | 8,500-9,500 |

The invention has now been described in such full, clear, concise and exact terms as to enable any person skilled in the art to which it pertains, to practice the same. It is to be understood that the foregoing describes preferred embodiments and examples of the invention and that modifications may be made therein without departing from the spirit or scope of the invention as set forth in the claims.

What is claimed is:

1. A cleansing composition comprising:
at least one surfactant;
at least one polyethylene glycol, polypropylene glycol derivative of glyceryl cocoate, or blends thereof; and
water.

2. The cleansing composition of claim 1, wherein the composition comprises at least one primary surfactant and at least one secondary surfactant.

3. The cleansing composition of claim 1, wherein the polyethylene glycol, polypropylene glycol derivative of glyceryl cocoate or blends thereof is present in the composition in an amount of about 0.1% to about 10% by weight of the total weight of the composition.

4. The cleansing composition of claim 3, wherein the polyethylene glycol, polypropylene glycol derivative of glyceryl cocoate is PEG/PPG-6/2 glyceryl cocoate.

5. The cleansing composition of claim 1, wherein the composition further comprises one or more additives selected from the group consisting of fragrances, colorants, skin conditioners, rheological modifiers, dyes, vitamins, herbal extracts, preservatives, opacifying agents, pearlescent agents, thickeners, emollients, foam builders, pH adjusters and anti-bacterial agents.

6. The cleansing composition of claim 2, wherein the primary surfactant is selected from the group consisting of anionic surfactants, amphoteric surfactants, non-ionic surfactants, cationic surfactants, zwitterionic surfactants, and mixtures thereof.

7. The cleansing composition of claim 6, wherein the primary surfactant is present in an amount of about 0.1% to about 70% by weight of the cleansing composition.

8. The cleansing composition of claim 2, wherein the secondary surfactant is present in an amount of about 0.1% to about 50% by weight of the cleansing composition.

9. The cleansing composition of claim 8, wherein the secondary surfactant is selected from the group consisting of betaines, amine oxides, hydroxysultaines, sulfosuccinates, amphoacetates, sarcosinates, and acyl lactylates.

10. The cleansing composition of claim 1, wherein the cleansing composition is clear.

11. A cleansing composition comprising:
(a) from about 0.1% to about 70% by weight of at least one surfactant;
(b) from about 0.1% to about 10% by weight of at least one polyethylene glycol, polypropylene glycol derivative of glyceryl cocoate or a blend thereof; and
(c) water.

12. The cleansing composition of claim 11, wherein the polyethylene glycol, polypropylene glycol derivative of glyceryl cocoate comprises an average of 6 moles of ethylene oxide and an average of 2 moles of propylene oxide incorporated into the glyceryl cocoate derivative.

13. The cleansing composition of claim 11, wherein the composition comprises at least one primary surfactant and at least one secondary surfactant.

14. The cleansing composition of claim 11, wherein the composition further comprises one or more additives selected from the group consisting of fragrances, colorants, skin conditioners, rheological modifiers, dyes, vitamins, herbal extracts, preservatives, opacifying agents, pearlescent agents, thickeners, emollients, foam builders, pH adjusters and anti-bacterial agents.

15. The cleansing composition of claim 13, wherein the primary surfactant comprises from about 0.1% to about 70% by weight of the cleansing composition, and the secondary surfactant comprises from about 0.1% to about 50% by weight of the cleansing composition.

16. The cleansing composition of claim 13, wherein the primary surfactant is selected from the group consisting of anionic surfactants, amphoteric surfactants, non-ionic surfactants, cationic surfactants, zwitterionic surfactants, and mixtures thereof.

17. The cleansing composition of claim 13, wherein the secondary surfactant is selected from the group consisting of betaines, amine oxides, hydroxysultaines, sulfosuccinates, amphoacetates, sarcosinates, and acyl lactylates.

18. The cleansing composition of claim 13, wherein the primary surfactant comprises from about 5% to about 60% by weight of the cleansing composition and the secondary surfactant comprises from about 1% to about 15% by weight of the cleansing composition.

19. The composition of claim 11, wherein the composition exhibits greater viscosity building than compositions free of polyethylene glycol, polypropylene glycol derivative of glyceryl cocoate or blends thereof.

20. The composition of claim 11, wherein the composition exhibits greater emulsion stability than compositions free of polyethylene glycol, polypropylene glycol derivative of glyceryl cocoate or blends thereof.

21. The composition of claim 11, wherein the compositions exhibits smaller oil droplet sizes in emulsion than compositions free of polyethylene glycol, polypropylene glycol derivative of glyceryl cocoate or blends thereof.

22. The composition of claim 11, wherein the compositions includes at least one salt or blend of salts at a concentration of from about 1% to about 2% based upon the total weight of the composition.

* * * * *